(12) United States Patent
Schmidt et al.

(10) Patent No.: US 10,168,346 B2
(45) Date of Patent: Jan. 1, 2019

(54) METHOD FOR DETERMINING THE PRESENCE OR ABSENCE OF DISPOSABLE PIPETTE TIPS IN PIPETTE TIP CARRIERS

(71) Applicants: TECAN TRADING AG, Mannedorf (CH); Werner Halg, Mannedorf (CH)

(72) Inventors: Martin Schmidt, Uznach (CH); Rainer Kerkmann, Mannedorf (CH)

(73) Assignee: TECAN TRADING AG, Mannedorf (CH)

( * ) Notice: Subject to any disclaimer, the term of this patent is extended or adjusted under 35 U.S.C. 154(b) by 0 days.

(21) Appl. No.: 15/310,269

(22) PCT Filed: Apr. 17, 2015

(86) PCT No.: PCT/EP2015/058440
§ 371 (c)(1),
(2) Date: Nov. 10, 2016

(87) PCT Pub. No.: WO2015/172971
PCT Pub. Date: Nov. 19, 2015

(65) Prior Publication Data
US 2017/0269115 A1    Sep. 21, 2017

(30) Foreign Application Priority Data

May 15, 2014 (CH) ....................... 0736/14

(51) Int. Cl.
*G01N 35/10* (2006.01)
*G01N 35/04* (2006.01)
*G01V 8/00* (2006.01)
*G06T 7/00* (2017.01)

(52) U.S. Cl.
CPC .......... *G01N 35/1011* (2013.01); *G01N 35/04* (2013.01); *G01V 8/00* (2013.01); *G06T 7/0008* (2013.01); *G01N 2035/0493* (2013.01); *G01N 2035/103* (2013.01); *G01N 2035/1013* (2013.01); *G06T 2207/10004* (2013.01); *G06T 2207/30164* (2013.01)

(58) Field of Classification Search
None
See application file for complete search history.

(56) References Cited

U.S. PATENT DOCUMENTS

2007/0177778 A1    8/2007  Massaro
2013/0065797 A1*   3/2013  Silbert ............... G01N 35/0099
                                                        506/39

(Continued)

*Primary Examiner* — Soo Shin
(74) *Attorney, Agent, or Firm* — Notaro, Michalos & Zaccaria P.C.

(57) ABSTRACT

A method for determining the presence or absence of disposable pipette tips in pipette tip carriers on the work area of a laboratory workstation. Each of the pipette tip carriers has a support panel with receiving holes into each of which a disposable pipette tip can be inserted. The laboratory workstation for carrying out the method has a robot arm with at least one pipette which is designed to receive and dispose of disposable pipette tips. The laboratory workstation has a digital camera which is arranged on a support device and is operatively connected to an analyzing unit. The work area of the laboratory workstation can be completely imaged in at least one first direction using the digital camera.

25 Claims, 3 Drawing Sheets

(56) References Cited

U.S. PATENT DOCUMENTS

2013/0280143 A1* 10/2013 Zucchelli ............... B25J 9/1697
       422/501
2013/0288873 A1   10/2013 Barbee et al.
2014/0036070 A1*  2/2014 Eckard ............... G06K 9/00624
       348/135
2017/0370956 A1* 12/2017 Hurwitz ............. G06K 9/00771

* cited by examiner

METHOD FOR DETERMINING THE PRESENCE OR ABSENCE OF DISPOSABLE PIPETTE TIPS IN PIPETTE TIP CARRIERS

The invention relates to a method for determining the presence or absence of disposable pipette tips in one or more selected pipette tip carriers on the work area of a laboratory work station. In this case, each of the selected pipette tip carriers comprises a preferably substantially horizontal carrier plate with a regular orthogonal arrangement of receiving holes. One disposable pipette tip can be inserted in each of these receiving holes. In addition, the laboratory work station comprises a robot arm with at least one pipette which is configured for receiving and delivering liquid samples and for receiving and discarding disposable pipette tips. In addition, the laboratory work station comprises a digital camera which is disposed on a carrier device and which is operatively connected to an evaluation unit, and with which the work area of the laboratory work station can be completely imaged at least in a first direction.

Such laboratory work stations are known and comprise, for example, a working surface or at least one work area for placement of laboratory articles such as, for example, containers in the form of microplates and sample tubes, supports or so-called "carriers" for receiving such containers or for example, pipette tips or pipette tip magazines or pipette tip carriers. These laboratory work stations preferably comprise a motorized robot or robot arm which can be fitted with grippers for gripping the laboratory article and/or with pipettes for receiving and delivering liquid samples. Specially preferred are those laboratory work stations which additionally comprise a processor or computer for controlling the movements of the motorized robot or robot arm and preferably also other parameters of the laboratory work stations. Laboratory work stations whose working surface or work areas are disposed substantially horizontally are preferred. Preferably a robot or robot arm configured as a pipetting robot comprises at least one pipette for receiving (aspirating) and delivering (dispensing) liquid samples and for receiving and discarding disposable pipette tips. Usually the controller of the laboratory work station is connected to the robot or robot arm and equipped with a corresponding software in such a manner that the processor causes the robot or robot arm to position a working tool, such as a pipette or a gripper, at determinable locations on the at least one work area, and to execute selected work there. Such laboratory work stations are known per se and are manufactured and distributed by the current applicant under the trade name Freedom EVO®.

A common feature of such laboratory work stations or systems is that samples are frequently processed in standardized microplates. Such microplates have been described and standardized by the American National Standards Institute (ANSI) and by the Society for Biomolecular Sciences (SBS). These microplates are available in all possible formats but typically comprise 96-sample vessels or wells which are arranged in a regular 8×12 grid with a 9 mm axial spacing. Microplates having a multiple (e.g. 384 or 1536) or only a part (e.g. 48 or 24) of this number of wells or density are also used. The distribution of wells in such microplates typically corresponds to the orthogonal arrangement of the disposable pipette tip in a preferred pipette tip carrier.

For example, one or more robots moving in accordance with a Cartesian coordinate system or a polar coordinate system can be used for working on a rectangular or round work area of a laboratory work station. A central control system or a computer monitors and controls these known laboratory systems whose exceptional advantage lies in the complete automation of the working processes. Consequently, such laboratory systems can be operated for hours and days without any human intervention being required.

The current applicant has filed for a patent for a method (cf. e.g. US 2014/0036070 A1) in which an arrangement of laboratory articles on a work area of a laboratory work station is detected by means of at least one reference digital image recorded with a digital camera. In this method a reference image parameter file is created by means of suitable selection and marking of visible features on the reference digital image and producing corresponding reference image sections. The reference digital images can be combined to form a reference overall image and used to compare a current arrangement of laboratory articles on a work area of a laboratory work station with a previously detected original arrangement of laboratory articles on the work area of this laboratory work station.

In pipetting, the operating reliability of a laboratory work station depends substantially on the availability of the pipette tips, in particular the disposable pipette tips on the work area of a laboratory work station.

It has been shown that it is very difficult to distinguish empty receiving holes from receiving holes occupied by disposable pipette tips of a receiving hole arrangement of a pipette tip carrier using a digital camera used according to the method in the application as already filed. A reason for this is that a digital camera always images a perspective, more or less optically distorted image of its surroundings. Thus, it can occur that an unoccupied receiving hole is covered by a disposable pipette tip placed in front of that or that a disposable pipette tip located behind an unoccupied receiving hole is visible through said unoccupied receiving hole. A reliable assessment of whether a specific receiving hole of a pipette tip carrier is actually occupied or empty is therefore not possible with the method known, for example, from US 2014/0036070 A1. In addition, the assessment is frequently made difficult by the fact that black disposable pipette tips are used in coloured (therefore rather dark) pipette tip carriers.

Another method for assessing whether a specific receiving hole of a pipette tip carrier is actually occupied or empty is based on pattern recognition (so called "pattern recognition") in which the images of occupied and empty receiving holes are compared with one another in relation of each individual receiving holes of a pipette tip carrier. In this case, each individual image must run through a certain sequence of image processing steps (Sobel transformation). Either a digital camera must be positioned with respect to each individual receiving hole of a pipette tip carrier so that its optical axis impinges perpendicularly on the pipette tip carrier; this causes a scanning of all the receiving holes of each of pipette tip carrier to be assessed, which on the one hand is very time-consuming and on the other hand requires a digital camera which can be moved in relation to two axes. Alternatively to this, a digital camera can be positioned on one side whereby several pipette tip carriers can be imaged simultaneously; then however perspective distortion must be expected. In addition, account must be taken of the circumstance that the disposable pipette tips do not sink completely into the pipette tip carrier and therefore project thereover and can cover empty receiving holes located therebehind. In addition, as already described, an unoccupied receiving hole can be covered by a disposable pipette tip placed in front thereof or a disposable pipette tip located behind an unoccupied receiving hole can be visible through said unoccupied receiving hole so that the influence of neighbouring disposable pipette tips can lead to difficult-to-interpret shadows and object edges. For these reasons a simple comparison of occupied and empty receiving holes of a pipette tip carrier using known image processing method cannot be recommended.

US 2013/0280143 A1 discloses devices and methods for the programmable handling of pipettes and for detecting whether available disposable pipette tips are located in a certain area on a pipette tip carrier to be marked out previously by hand using identification marks. Whether a disposable pipette tip is located in a specific receiving hole of a pipette tip carrier or not cannot be determined with this method.

US 2013/0288873 A1 discloses a device for amplification of nucleic acid samples (PCR) and loading arrays with such samples. The device comprises a robot arm which can be moved in all three spatial directions for receiving a pipette and for receiving and delivering liquid samples with this pipette and a pipette tip carrier. The system can comprise an optical sensor by means of which it is determined, for example, whether a pipette tip has been fastened to the pipette or successfully discarded therefrom. The device can use a camera for checking the presented consumables and, for example, photograph a rack. The device can analyze these photographs and thereby identify features in the image such as, for example, circular shapes of tubes or pipette tips. By analyzing the filtered photographs, the presence or absence of a sample tube or a pipette tip in the arrangement of an address array can be determined. If an error is detected, the user can be warned.

US 2013/0065797 A1 discloses an automated sample processing station with an automatic real-time inventory system for consumables. The creation of an inventory for pipette tips and waste bins is disclosed: a camera is fastened to the device such that this can see the laboratory table and can take photographs of the pipette tip carrier and waste bins. By means of image processing methods, a complete inventory of all the pipette tips in the pipette tip carrier and waste bins is determined. The camera can also be fastened to the robot arm. The inventory system monitors the number of pipette tips present in the pipette tip carriers.

The object of the present invention is to provide an alternative method which enables a laboratory work station to reliably but simply determine the number and position of the disposable pipette tips available on the work area of a laboratory work station.

This object is solved by the method according to the invention comprising the features of the independent claim 1. This initially presented method for determining the presence or absence of disposable pipette tips in selected pipette tip carriers on the work area of a laboratory work station comprises using an evaluation unit and the following working steps, in which by using the evaluation unit:

a) pipette tip carriers arranged on the work area of a laboratory work station are selected;
b) at least one digital image with a plurality of pixels is taken of each selected pipette tip carrier using the digital camera;
c) in relation to at least one digital image of each selected pipette tip carrier, a grid consisting of grid elements is defined on the respective pipette tip carrier, wherein the grid is spanned by the four outermost receiving holes of the receiving hole arrangement.

The method according to the invention is characterized in that the grid is an originally orthogonal grid with square grid elements adapted perspectively to the digital image, wherein:

d) in at least one digital image of each selected pipette tip carrier, pixel areas which can be assigned to the individual grid elements are determined, whereby each grid element of the defined grid is divided into four quadrants;
e) in each of the determined pixel areas of a digital image the respective number of pixels whose brightness lies in a predetermined range is determined; and
f) it is determined that a disposable pipette tip is present or not in a specified receiving hole of a pipette tip carrier when the number of pixels determined in step e) lies in a selected range relative to a predetermined threshold value.

Preferred embodiments and further inventive features are obtained from the dependent claims. In particular, it is preferred that two digital images of each selected pipette tip carrier with a plurality of pixels are recorded with the digital camera, wherein:

i) a first digital image serves as reference image and is used to determine the actual positions of the four outermost receiving holes as well as threshold values for the low-brightness pixels; and
ii) a second digital image serves as run-time image and is used to determine which receiving holes are occupied by disposable pipette tips.

The method according to the invention is explained in detail with reference to the appended figures, where these figures show at least in some cases highly schematic and in any case selected exemplary embodiments and are not intended to delimit the disclosure content in relation to the present invention. In the figures.

Figure 1:
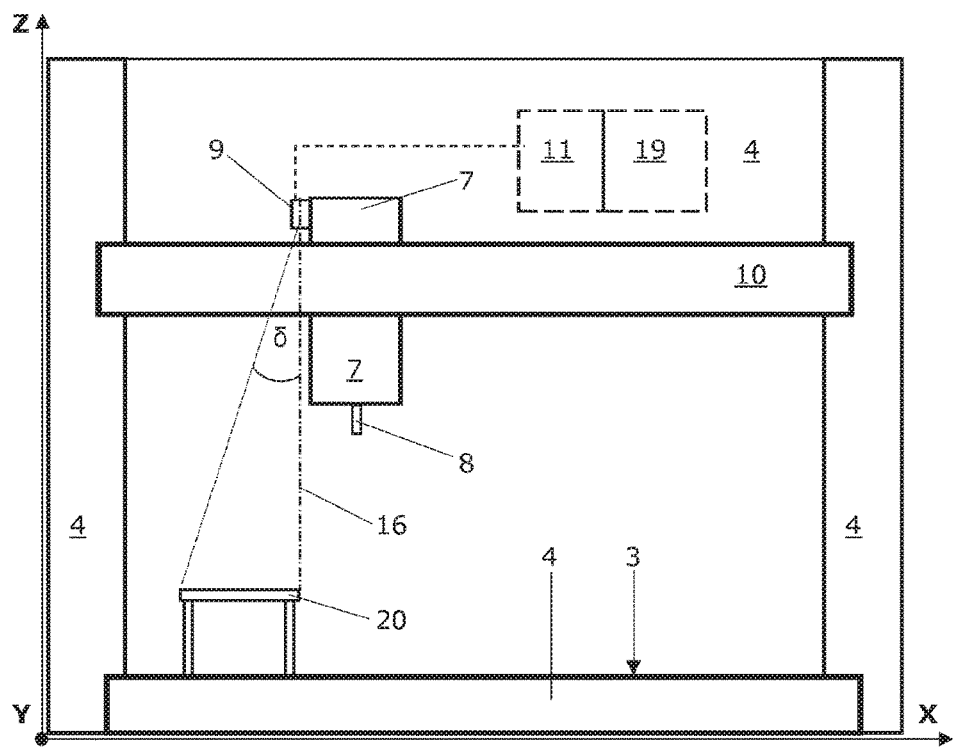
FIG. 1 shows a schematic front view of a laboratory work station with a digital camera fastened to a robot arm and with a carrier for three pipette tip carriers; the minimal half field of view of the digital camera in the X direction of the Cartesian coordinate system is given in relation to the optical axis of the digital camera.

The method according to the invention for determining the presence or absence of disposable pipette tips 1 in selected pipette tip carriers 2 on the work area 3 of a laboratory work station 4 is now presented with reference to the appended figures. FIG. 1 shows a schematic front view of a laboratory work station 4 which is suitable for carrying out the method according to the invention. A digital camera 9 and a carrier 20 for three pipette tip carriers 2 (not visible here) are fastened to a robot arm 7 of this laboratory work station 4. The minimal half field of view of the digital camera 9 in the X direction of the Cartesian coordinate system typical for this preferred laboratory work station 4 is given in relation to the optical axis 16 of the digital camera 9. In this case, the two axes X and Y define a substantially (i.e. within the limits of manufacturing accuracy) horizontal plane which is spanned between the X and Y axes of a Cartesian coordinate system and the Z axis is substantially perpendicular (i.e. within the limits of manufacturing accuracy) to this horizontal plane.

Figure 4:
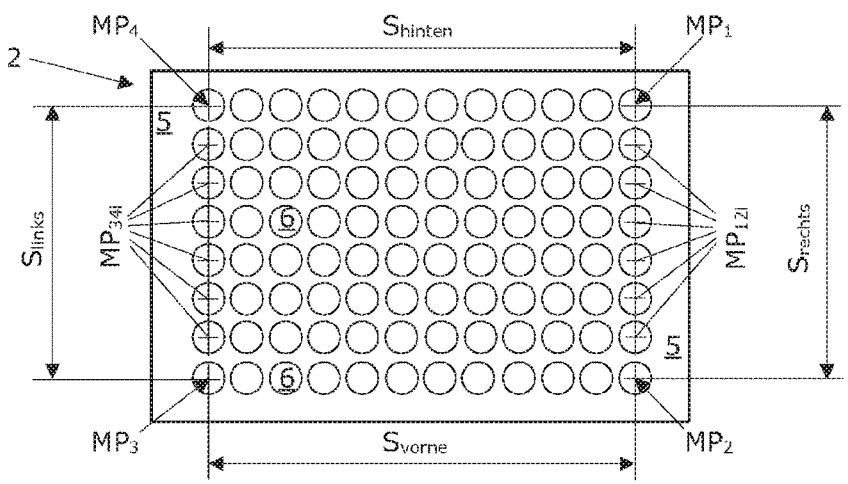
FIG. 4 shows a schematic plan view of a 96 pipette tip carrier with an exemplary view of the central points of the outermost receiving holes 6' of a pipette tip carrier 2 and the calculated central points $MP_{12i}$ and $MP_{34i}$.
Figure 5:
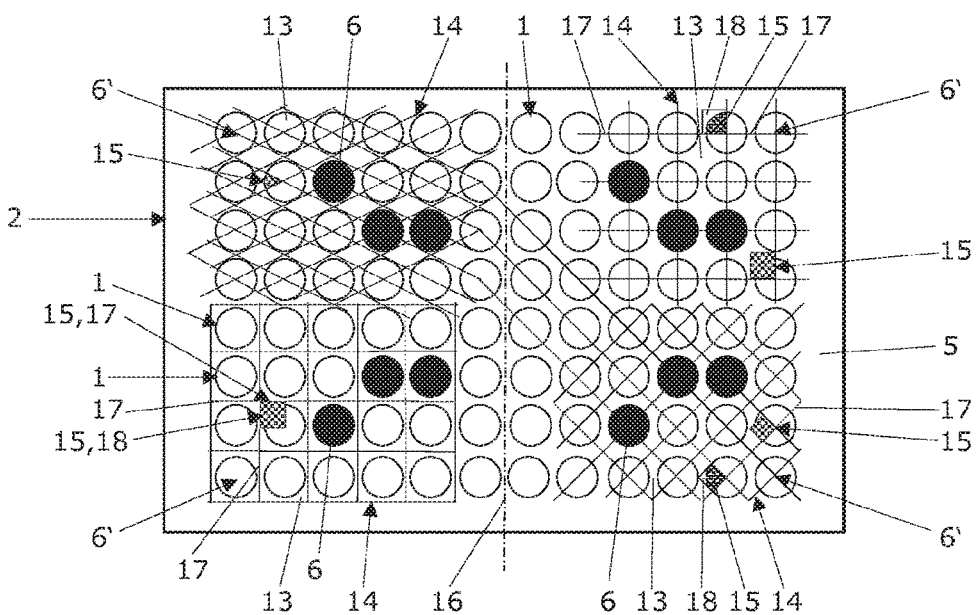
FIG. 5 shows a schematic plan view of a 96 pipette tip carrier with some inserted disposable pipette tips, exemplary grids and specific pixel areas.

Each of the selected pipette tip carriers 2 has a carrier plate 5 with a regular orthogonal arrangement of receiving holes 6 in which respectively one disposable pipette tip 1 can be inserted (cf. FIGS. 4 and 5). The laboratory work station 4 comprises the robot arm 7 with at least one pipette 8. This pipette 8 is configured for receiving and delivering liquid samples and for receiving and discarding disposable pipette tips 1. The laboratory work station 4 additionally comprises a digital camera 9 which is disposed on a carrier device 10 and which is operatively connected to an evaluation unit 11 and with which the work area 3 of the laboratory work station 4 can be completely imaged at least in one direction. On the carrier device 10 shown here the robot arm 7 is movable in a motorized manner (drive is not shown here) in the X direction of the Cartesian coordinate system. The at least one pipette 8 of the robot arm 7 can be moved for receiving a disposable pipette tip 1 in the direction of the Z axis of the laboratory work station 4. The at least one pipette 8 can be moved by means of the robot arm 7 before receiving or discarding a disposable pipette tip 1 but also for receiving (aspirating) and delivering (dispensing) a liquid volume in the direction of the Y and Z axis of the laboratory work station 4, preferably in its entire work area 3.

Unlike this exemplary embodiment, the digital camera 9 could also be fastened directly to the carrier device 10 and immovably; then however the imaging of the pipette tip carriers 2 would be restricted to the immovable field of view of this digital camera 9. Alternatively to a digital camera 9 movable by means of the robot arm 7, a plurality of digital cameras 9 could also be fastened immovably to the carrier device 10 such that a multiple of the field of view of a single digital camera 9 would be available for imaging of pipette tip carriers 2 (not shown). For example, two digital cameras 9 could be fastened to the robot arm 7 such that the one on the left (as shown) and the other on the right (not shown) of the robot arm 7 would be available for imaging the pipette tip carriers 2. If the work area 3 of the laboratory work station 4 in the Y direction (cf. FIG. 2) would have such a large extension that this could not be completely imaged by a single digital camera 9 in the Y direction, two or more digital cameras 9 with different fields of view can also be used with the aim of completely imaging the work area 3 of the laboratory work station 4 at least in this first direction.

Preferably, the robot arm 7 of the laboratory work station 4 is moved in the direction of the X axis and/or the Y axis for recording the digital images 12 with the digital camera 9. Especially preferably, the robot arm 7 of the laboratory work station 4 is moved into a specific X position in relation to a selected pipette tip carrier 2 for recording the digital images 12 with the digital camera 9.

Figure 2:
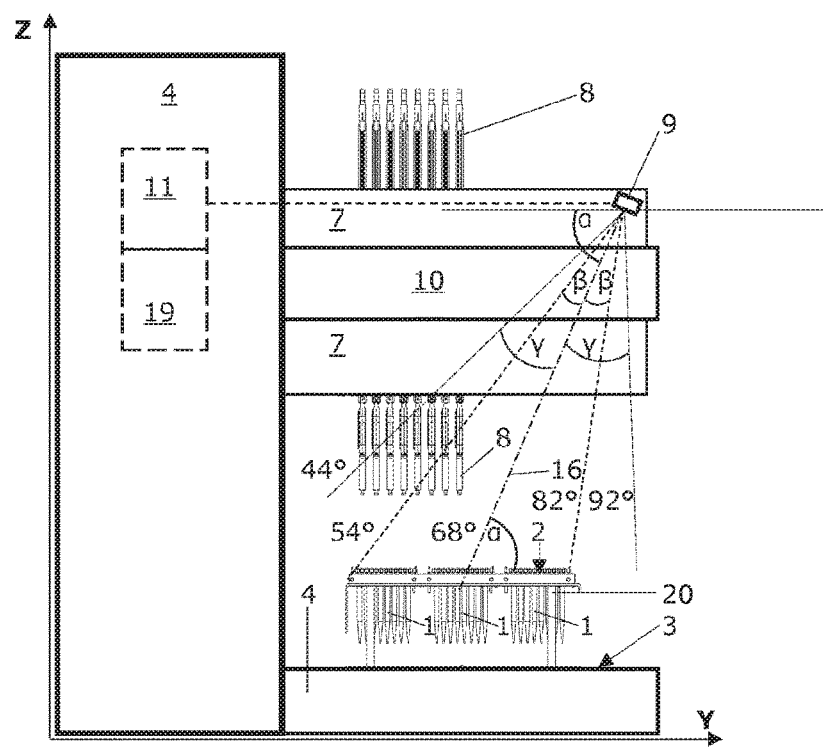
FIG. 2 shows a schematic side view of the laboratory work station of FIG. 1 with depicted arrangement of the pipettes on the robot arm and the carrier with three pipette tip carriers; the minimal and the preferred field of view of the digital camera in the Y direction of the Cartesian coordinate system is given in relation to the optic axis of the digital camera.

In the exemplary embodiment of a laboratory work station 4 shown in FIGS. 1 and 2, the robot arm 7 of the laboratory work station 4 is simultaneously configured as a carrier device 10 for the one digital camera 9. Preferably, the digital camera 9 has a field of view which differs in the X direction of the Cartesian coordinate system by at least an angle δ (cf. FIG. 1). The angle δ is here preferably 18°.

FIG. 2 shows a schematic side view of the laboratory work station 4 of FIG. 1 with depicted arrangement of the eight pipettes 8 on the robot arm 7 and the carrier 20 with three pipette tip carriers 2. In these three 96 pipette tip carriers 2 disposable pipette tips 1 with a capacity of 200 µl are shown. The robot arm 7 here carries eight pipettes 8 which can all be moved individually, in groups or jointly in the Z direction. The minimal and the preferred field of view of the digital camera 9 in the Y direction of the Cartesian coordinate system is given in relation to the optical axis 16 of the digital camera 9. This digital camera 9 has an optical axis 16 which passes through the carrier plate 5 of the pipette tip carrier 2 disposed on the work area 3 of the laboratory work station 4 at an angle α. This angle α preferably lies in a range of 40° to 90°, particularly preferably in a range of 55° to 90°. Especially preferably and as shown in FIG. 2, the angle α is 68°. In this example the condition holds that the digital camera is inclined with respect to the horizontal by 22° and that the pipette tip carriers 2 are arranged horizontally. Preferably, the digital camera 9 has a field of view which in the Y direction of the Cartesian coordinate system differs by at least an angle β, preferably by an angle γ (cf. FIG. 2). In this case, the angle β is preferably 14° and the angle γ is preferably 24°.

Figure 3A:
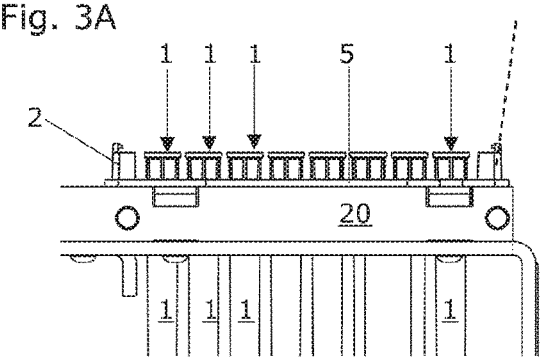
FIG. 3A shows a detailed section from the side view of FIG. 2 with eight disposable pipette tip shown in the view of a 96 pipette tip carrier with indicated limit of the minimal field of view of the digital camera.

FIG. 3A shows a detailed section from the side view of FIG. 2 with eight disposable pipette tips 1 of a 96 pipette tip carrier 2 as shown in the view with indicated limit (dashed line) of the minimal field of view of the digital camera 9. The pipette tip carrier 2 is preferably received in a carrier 20 (i.e. in a carrier unit 20) such that the carrier plate 5 for the disposable pipette tips 1 is arranged substantially horizontally. The so-called collars of the disposable pipette tips 1 can be clearly seen here, which are configured as lateral webs which support the disposable pipette tip 1 on the carrier plate 5 and prevent the disposable pipette tips 1 from falling through the respective receiving holes 6 (cf. FIG. 3B).

Figure 3B:
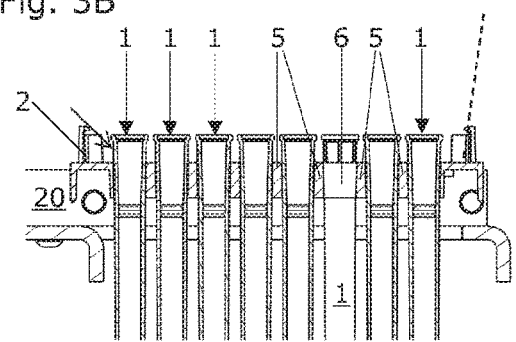
FIG. 3B shows a detailed vertical section corresponding to the side view of FIG. 3A through seven of the eight disposable pipette tips with indicated limit of the minimal field of view of the digital camera.

FIG. 3B shows a detailed vertical section corresponding to the side view of FIG. 3A through seven of the eight disposable pipette tips 1 of a 96 pipette tip carrier 2 with indicated limit (dashed line) of the minimal field of view of the digital camera 9. In the sixth position counted from the left, a disposable pipette tip 1 is missing so that the receiving hole 6 is empty and the disposable pipette tip 1 in the next row can be seen in the view. A lateral web of the collar of the disposable pipette tip 1 in the first position from the left is marked here with an open arrow. Preferably, the evaluation unit 11 is operatively connected to a controller 19 of the laboratory work station 4 or integrated in this controller 19.

After the preferred embodiments of the laboratory work station 4 to be used and the optical boundary conditions have been explained in detail, the method according to the invention will be presented in detail. By using the evaluation unit 11, the following work steps are carried out:

a) pipette tip carriers 2 arranged on the work area 3 of a laboratory work station 4 are selected. This selection is made easier by the robot arm 7 with the digital camera 9 fastened thereon being positioned such that all the pipette tip carriers 2 of a carrier 20 set up in the work area 3 of the laboratory work station 4 are located in the field of view of the digital camera 9. In order to allow any vibrations of the mechanical system to die down, a short pause is preferably inserted before the next step.

b) at least one digital image 12 with a plurality of pixels is taken of each selected pipette tip carrier 2 using the digital camera 9 and monitored in relation to exposure and contrast. If necessary, the exposure parameters of the digital camera are corrected and further digital images 12 are recorded until an acceptable digital image 12 is present or a previously defined number of unsuccessful recording attempts is exceeded (in the latter case the process is discontinued). Alternatively (but not particularly preferably) an analogue camera can also be used but its images must then be digitized).

c) in relation to at least one digital image 12 of each selected pipette tip carrier 2, a grid 14 consisting of grid elements 13 is defined on the respective pipette tip carrier 2, wherein the grid 14 is spanned by the four outermost receiving holes 6' of the receiving hole arrangement. If for example, three pipette tip carriers 2 are imaged on a digital image 12, the four outermost receiving holes 6' of each individual pipette tip carrier 2 each define an individual grid 14 so that three individual grids 4 are defined in this example. Alternatively (but not particularly preferably), four arbitrary central points, preferably spaced as far apart from one another as possible, of receiving holes 6, 6' are used to define the grid 14.

As a result of the equidistant arrangement of the receiving holes 6. 6', all the central points of all the receiving holes 6 can be calculated from the central points of the four outermost receiving holes 6; under the following conditions:

The origin in the coordinate system used is located outside the digital image 12 on the top left;

The number of receiving holes 6, 6' in the horizontal direction ($AL_H$) and vertical direction ($AL_V$) is known.

Each point ($MP_i$) represents a coordinate which can be expressed by two components of the form P(x, y).

$MP_1$ corresponds to the central point of the right rear outer receiving hole 6'.

$MP_2$ corresponds to the central point of the right front outer receiving hole 6'.

$MP_3$ corresponds to the central point of the left front outer receiving hole 6'.

$MP_4$ corresponds to the central point of the left rear outer receiving hole 6' (cf. FIGS. 4 and 5).

i) The following distances S of the central points of the four outermost receiving holes 6' are obtained:

$$S_{right} = MP_{2(Y)} - MP_{1(Y)}$$

$$S_{front} = MP_{2(X)} - MP_{3(X)}$$

$$S_{left} = MP_{3(Y)} - MP_{4(Y)}$$

$$S_{rear} = MP_{1(X)} - MP_{4(X)}$$

Wherein $MP_{i(Y)}$ is the Y component of the points $MP_i$ and $MP_{i(x)}$ is the X component of the points $MP_i$.

ii) The central points of all the outer receiving holes 6' can be calculated from the distances S, the alignment R of the pipette tip carrier 2 and the number of receiving holes 6, 6' in the horizontal direction $AL_H$ and vertical direction $AL_V$:

$$MP_{12i} = S_{right}/AL_V$$

$$MP_{23i} = S_{front}/AL_H$$

$$MP_{34i} = S_{left}/AL_V$$

$$MP_{41i} = S_{rear}/AL_H$$

Here it holds that:

$MP_{12i}$=distances of the central points of the receiving holes 6, 6' along the connecting line between MP1 and MP2

$MP_{23i}$=distances of the central points of the receiving holes 6, 6' along the connecting line between MP2 and MP3

$MP_{34i}$=distances of the central points of the receiving holes 6, 6' along the connecting line between MP3 and MP4

$MP_{41i}$=distances of the central points of the receiving holes 6, 6' along the connecting line between MP4 and MP1.

Figure 7:
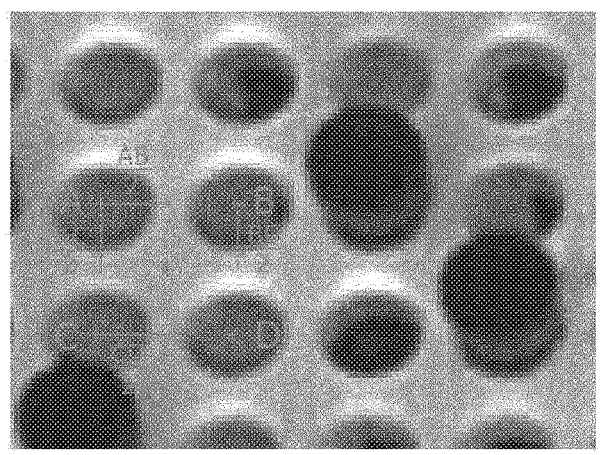
FIG. 7 shows an exemplary view for determining a corner point of any grid element by reference to four surrounding central points.

FIG. 4 contains an exemplary diagram of the central points of the outermost receiving holes 6' of a pipette tip carrier 2 and the calculated distances of the central points $MP_{12i}$ and $MP_{34i}$.

iii) Using the results from ii), the central points of all the other receiving holes can be calculated according to the procedure in ii).

iv) In order to calculate a corner point of a grid element, half the distance between two neighbouring central points from iii) is calculated in the same direction x or y. For each direction x and y as a result of the non-uniformity of the quadrilateral on the digital image 12 which is produced by the central points, it is necessary to determine the half-distance on each side of the quadrilateral. The resulting positions of the half-distance are used as points of two lines whose point of intersections gives the corner point of a grid element. FIG. 7 contains the exemplary view for determining a corner point (green) of an arbitrary grid element by means of four surrounding central points (orange) from c). In general, the points A and B, B and D, D and C, C and A are corner points of a triangle so that the half-distances AB/2, BD/2, CD/2 and AC/2 do not only depend on one direction but on two (X and Y).

d) in at least one digital image 12 of each selected pipette tip carrier 2, pixel areas 15 which can be assigned to the individual grid elements (13) are determined. A two-dimensional pixel area 15 (area) is obtained from respectively four corner points of a grid element 13. A one-dimension pixel area (line) is obtained by applying the Bresenham algorithm to two neighbouring corner points in the horizontal direction in order to determine the points which lie on the connecting line between two neighbouring corner points in the horizontal direction.

e) In each of the determined pixel areas 15 of a digital image 12 the respective number of pixels whose brightness lies in a predetermined range is determined. The threshold value or range for the brightness of the pixels is determined under the following conditions:

v) Black disposable pipette tips 1 having a brightness $H_{DiTi}$ and pipette tip carriers 2 are used, whose brightness $H_{Tray}$ under the same conditions and light ratios on a recorded image is significantly greater than $H_{DiTi}$, where the brightnesses are expressed by the values of the three colour components red, green, blue of a pixel or by the average values of the three colour components red, green, blue of an adequate pixel area in the RGB colour space.

vi) Empirical determination of the threshold values: Since as a result of the conditions on the pipette tip carrier 2, there cannot be any darker pixel areas than the pixel areas caused by the disposable pipette tips 1, only the threshold value is important. The lower limit in the range is 0 in each case.

f) It is determined that a disposable pipette tip 1 is present or not in a specified receiving hole 6 of a pipette tip carrier 2 when the number of pixels determined in step e) lies in a selected range relative to a predetermined threshold value.

A threshold value having a brightness weakness=21 is assumed for the evaluation of a two-dimensional pixel area (quadrant 18). In this case, 60% of the pixel area 15 must be filled with low-brightness pixels. For the evaluation of a one-dimensional pixel area (grid line 17) a threshold value with a brightness weakness=25 is assumed. In this case, 40% of the pixel area 15 must be filled with low-brightness pixels.

For a heuristic determination of the threshold value, the digital image 12 must contain a pixel area in which a disposable pipette tip 1 is placed in a receiving hole 6, 6' of a pipette tip carrier 2. This is followed by generating the grid (cf. step c) above) and a brightness analysis for each quadrant 18 in the grid 14 except for the four outermost receiving holes 6':

vii) For calculation of the threshold value, that quadrant 18 in which the average brightness is lowest is used, since the disposable pipette tip 1 is located in this quadrant under the conditions applied in i). The threshold value is obtained from the sum of the average brightness of the quadrant 18 with an empirical correction factor which takes into account any reflections on the shiny surface of the disposable pipette tip.

viii) The threshold value along the adjoining grid line 17 can be obtained from vii).

It can be quite sufficient to carry out steps c), d) and e) according to the invention for a single digital image 12 per pipette tip carrier 2. However, it has proved advantageous to record two digital images 12 of each selected pipette tip carrier 2 with a plurality of pixels with the digital camera 9, wherein:

a first digital image 12 serves as reference image and is used to determine the actual positions of the four outermost receiving holes 6' as well as threshold values for the low-brightness pixels; and a second digital image 12 serves as run-time image and is used to determine which receiving holes 6 are occupied by disposable pipette tips 1.

Both in the reference image and also in the run-time image or measurement image, the individual pipette tip carrier 2 is selected by its four corner points (central points of the outermost receiving holes 6') in the evaluation software. If for example three pipette tip carriers 2 are on the image, 3 times 4 corner points are defined.

FIG. 5 shows a schematic plan view of a 96 pipette tip carrier 2 with several inserted disposable pipette tips 1, with exemplary grids 14 and with specific pixel areas 15. Also marked on this pipette tip carrier 2 are the four outermost receiving holes 6' which span this grid 14. The preferred profile of the optic axis 16 of the digital camera is indicated at least approximately in FIG. 4. As depicted as an example, these grids can have an orthogonal structure and their grid lines 17 can run parallel to the edges of the pipette tip carrier 2 (cf. bottom left and top right). In the digital image 12 (cf. FIG. 6) the grid 14 is preferably an originally orthogonal grid with square grid elements (13) adapted perspectively to this digital image 12.

In this case, for example, the points of intersection of the grid lines 17 can lie at the centre of the receiving holes 6, 6' (cf. top right). Here, preferably those pixel areas 15 are determined which (as shown) are defined by the respectively lower right quadrants 18 of a grid element 13 or which lie on those grid lines 17 which adjoin these quadrants 18 and run through the centres of the twelve receiving holes 6, 6' of a row.

Alternatively, the central point of the grid elements 13 can lie in the centre of the receiving holes 6, 6' (cf. bottom left) such that the receiving holes 6, 6' are framed by the grid lines 17. Here, preferably those pixel areas 15 are determined which (as shown) are defined by the respectively upper left quadrants 18 of a grid element 13 or which lie on those grid lines 17 which adjoin these quadrants 18 and are arranged parallel to the twelve receiving holes 6, 6' of a row.

Alternatively, an orthogonal grid 14 can be defined for example such that its grid lines 17 run at an angle of 45° to the edges of the pipette tip carrier 2 (cf. bottom right). Here, preferably those pixel areas 15 are determined which (as shown) are defined by the respectively right quadrants 18 of a grid element 13 or which lie on those grid lines 17 which adjoin these quadrants 18 and run through the receiving holes 6, 6'. Instead of the variant shown with the points of intersection of the grid lines 17 in the centre of the receiving holes 6, 6' the grid lines 17 could also frame the receiving holes 6, 6' (not shown).

In addition, the pixel areas can be defined—at least approximately—as the (circular-sector-shaped) cut set of a quadrant 18 with a circle of a receiving hole 6, 6' of the pipette tip carrier 2 (cf. right at the top and bottom right in FIG. 5).

Preferably such an orthogonal grid comprises square grid elements 13 because an optimal agreement of the grid 14 with the orthogonal arrangement of the receiving holes 6, 6' of a pipette tip carrier 2 can thus be achieved. However grids other than orthogonal are also feasible and can be used; for the purpose of demonstrating one of many alternative possibilities (cf. top left) a rhombic grid 14 is shown here whose grid lines 17 intersect in the centres of the receiving holes 6, 6'. Here preferably those pixel areas 15 would be determined which lie in the right-hand corner of the rhombi which connect two centres of neighbouring receiving holes 6, 6'.

It is preferred that each grid element 13 of the defined grid 14 is divided into four quadrants 18 and in each case one quadrant 18 of each grid element 13 is determined as pixel area 15. Preferably, the two-dimensional pixel area 14 determined in step d) is in each case the left rear quadrant 18 of each grid element 13 in the direction of the optical axis 16 when viewed from the digital camera 9 (cf. FIG. 5, bottom left).

It is preferred that each grid element 13 of the defined grid 14 is divided into four quadrants 18 and in each case one grid line 17 of each grid element 13 adjoining this quadrant 18 is determined as pixel area 15. Preferably the one-dimensional pixel area 15 determined in step d) is in each case the rear grid lines 17 of the left rear quadrant adjoining each of the selected quadrants 18 in the direction of the optic axis 16 when viewed from the digital camera 9 (cf. FIG. 5, bottom left).

FIG. 2 shows the extreme angles for the frontmost and rearmost pipette tip carriers 2 of a carrier 20. In this embodiment of a preferred laboratory work station 4 the digital camera 9 always looks onto the disposable pipette tips 1 from the left so that preferably the left upper quadrant 18 is selected for the image evaluation (cf. FIG. 4). Preferably the viewing angle differences between the left and right sides of the pipette tip carrier 2 are small and play no role or a negligible role for the evaluation.

Alternatively and nevertheless in the sense of the present invention, the desired pixel areas 15 can be determined in any grid elements 13 of an arbitrarily defined grid 14 with the aid of a mask. Preferably a pixel area 15 is determined in each grid element 13 of the defined grid 14 with the aid of a mask.

It is especially preferred that in each of the determined pixel areas 15 of a digital image 12, the number of all the low-brightness pixels is determined and that it is established that a disposable pipette tip 1 is present in a selected receiving hole 6 of a pipette tip carrier 2 if the number of pixels determined in step e) is the same as or higher than a respectively predetermined threshold value.

It can also be selected that in each of the determined pixel areas 15 of a digital image 12, the number of all the low-brightness pixels is determined and that it is established that no disposable pipette tip 1 is present in a selected receiving hole 6 of a pipette tip carrier 2 if the number of pixels determined in step e) is smaller than a respectively predetermined threshold value. Combinations of these two procedures are also possible.

Figure 6:
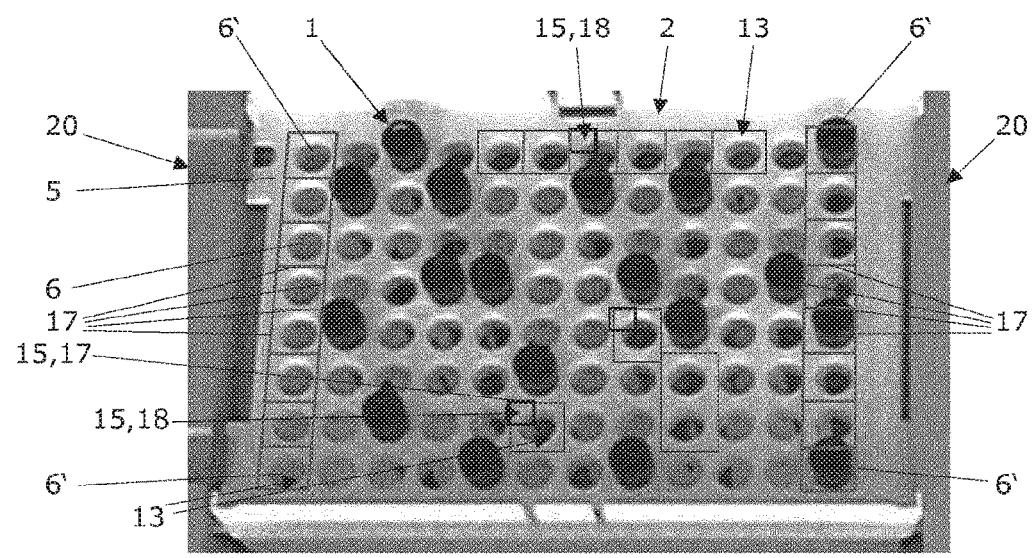
FIG. 6 shows a digital image of a 96 pipette tip carrier which is carried by a carrier device and which has receiving holes occupied by disposable pipette tip and unoccupied receiving holes.

FIG. 6 shows an exemplary digital image 12 of a 96 pipette tip carrier 2 which is carried by a carrier unit 20, i.e. by a carrier 20 and which has receiving holes 6, 6' occupied by disposable pipette tips 1 and unoccupied receiving holes. Individual grid elements 13 of a grid 14 (cf. FIG. 5, bottom left) are indicated. Exemplary two-dimensional pixel areas 15 determined as quadrants 18 and one-dimensional pixel areas 15 determined as grid lines 17 are also marked (cf. FIG. 5, bottom left). It is particularly clear from the indicated grid lines 17 which cover the first and twelfth column of the receiving holes 6, 6' of the pipette tip carrier 2 that the originally orthogonal grid 14 in this digital image 12 is perspectively adapted to this digital image.

Depending on the dimension and size of chassis and robot arm 7 of a laboratory work station 4, the position of one or more digital cameras 9 must be redefined. A greater length of carriers 20 must possibly be compensated by a central attachment of the digital camera 6 and situative selection of the quadrant 18 on the digital images 12. In general the digital camera 9 should be attached sufficiently high so that the algorithm functions for the highest carrier 20. For lower carriers 20 the field of view of the digital camera 9 is larger and therefore less problematic. In general it is preferred that the digital camera 9 is attached so that it can cover all the pipette tip carriers 2 of the carrier 20 with only one image; to this end the digital camera 9 must be driven only with the robot arm 7 into the suitable X position.

The same reference numbers in the figures correspond to the same features even if these are not described in detail in each case. The X direction and Y direction of the Cartesian coordinate system are specified such that these are defined in a preferred laboratory work station 4; naturally and in relation to other laboratory work stations 4 these two directions arranged at right angles to one another could also be exchanged with one another. Preferably the shape of the carrier plate 5 corresponds to the shape of a standard microplate according to the SBS standard.

REFERENCE LIST

1 Disposable pipette tip
2 Pipette tip carrier
3 Work area
4 Laboratory work station
5 Carrier plate
6 Receiving hole
6' Outermost receiving hole
7 Robot arm
8 Pipette
9 Digital camera
10 Carrier device
11 Evaluation unit
12 Digital image; reference image; run-time image
13 Grid element
14 Grid
15 Pixel area
16 Optical axis of 9
17 Grid lines
18 Quadrant
19 Controller of 4
20 Carrier, carrier unit

The invention claimed is:

1. A method for determining presence or absence of disposable pipette tips (1) in selected pipette tip carriers (2) on the work area (3) of a laboratory work station (4), wherein each of the selected pipette tip carriers (2) comprises a carrier plate (5) with an orthogonal arrangement of receiving holes (6), in which respectively one disposable pipette tip (1) can be inserted, wherein the laboratory work station (4) comprises a robot arm (7) with at least one pipette (8), which is configured for receiving and delivering liquid samples and for receiving and discarding disposable pipette tips (1), and wherein the laboratory work station (4) comprises a digital camera (9) which is disposed on a carrier device (10) and which is operatively connected to an evaluation unit (11), and with which the work area (3) of the laboratory work station (4) can be completely imaged at least in a first direction, wherein by using the evaluation unit (11):
   a) the pipette tip carriers (2) arranged on the work area (3) of the laboratory work station (4) are selected;
   b) at least one digital image (12) with a plurality of pixels is taken of each of the selected pipette tip carriers (2) using the digital camera (9);
   c) in relation to the at least one digital image (12) of each of the selected pipette tip carriers (2), a grid (14) consisting of grid elements (13) is defined on the respective pipette tip carrier (2), wherein the grid (14) is spanned by the four outermost receiving holes (6') of an arrangement of receiving holes; characterized in that the grid (14) is an orthogonal grid with square grid elements (13) adapted perspectively to the at least one digital image (12), wherein:
   d) in relation to the at least one digital image (12) of each of the selected pipette tip carriers (2), pixel areas (15) which can be assigned to the grid elements (13) are determined, whereby each of the grid elements (13) of the grid (14) is divided into four quadrants (18);
   e) in each of the determined pixel areas (15) of the at least one digital image (12) a respective number of pixels whose brightness lies in a predetermined range is determined; and
   f) determining whether the disposable pipette tip (1) is present or absent in one of the receiving holes (6) of the selected pipette tip carriers (2) when the number of pixels determined in step e) lies in the predetermined range relative to a predetermined threshold value.

2. The method according to claim 1, characterized in that two digital images (12) of each of the selected pipette tip carriers (2) with a plurality of pixels are recorded with the digital camera (9), wherein:
   i) a first digital image serves as reference image and is used to determine actual positions of the four outermost receiving holes (6') as well as threshold values for low-brightness pixels; and ii) a second digital image serves as run-time image and is used to determine which of the receiving holes (6) are occupied by the disposable pipette tips (1).

3. The method according to claim 1, characterized in that the digital camera (9) has an optical axis (16), which passes through the carrier plate (5) of the selected pipette tip carriers (2) disposed on the work area (3) of the laboratory work station (4) at a first angle, wherein the first angle is in a range of 40° to 90° and especially preferably is 68°.

4. The method according to claim 1, characterized in that the grid (14) with its grid lines (17) is defined on the selected pipette tip carriers (2) such that:
   (i) points of intersection of the grid lines (17) lie at the centre of the receiving holes (6); or
   (ii) the receiving holes (6) are framed by the grid lines (17).

5. The method according to claim 1, characterized in that one of the quadrants (18) of each of the grid elements (13) is defined as the determined pixel areas (15).

6. The method according to claim 1, characterized in that one of the grid lines (17) of each of the grid elements (13) adjoining one of the quadrants (18) is determined as the determined pixel areas (15) respectively.

7. The method according to claim 1, characterized in that the determined pixel areas (15) are determined in each of the grid elements (13) of the grid (14) by means of a mask.

8. The method according to claim 1, characterized in that the determined pixel areas (15) are defined at least approximately as a cut set of one of the four quadrants (18) with a circle of the receiving holes (6) of the selected pipette tip carriers (2).

9. The method according to claim 1, characterized in that in each of the determined pixel areas (15) of the at least one digital image (12) a number of all low-brightness pixels is determined, and that the presence of the a disposable pipette tips (1) in the receiving holes (6) of the selected pipette tip carriers (2) is determined, if the number of pixels determined in step e) is the same as or higher than a respectively predetermined threshold value.

10. The method according to claim 1, characterized in that in each of the determined pixel areas (15) of the at least one digital image (12) a number of all low-brightness pixels is determined, and that the absence of the disposable pipette tips (1) in the receiving holes (6) of the selected pipette tip carriers (2) is determined if the number of pixels determined in step e) is less than a respectively predetermined threshold value.

11. The method according to claim 9, characterized in that the number of all low-brightness pixels of the pixel areas (15) of the at least one digital image (12) is determined.

12. The method according to claim 1, characterized in that the robot arm (7) of the laboratory work station (4) is simultaneously configured as the carrier device (10) for the digital camera (9).

13. The method according to claim 1, characterized in that the work area (3) of the laboratory work station (4) forms a horizontal plane which is spanned between the X and Y axes of a Cartesian coordinate system.

14. The method according to claim 13, characterized in that the robot arm (7) of the laboratory work station (4) is moved in the direction of the X axis and/or the Y axis for recording the at least one digital image (12) with the digital camera (9).

15. The method according to claim 14, characterized in that the robot arm (7) of the laboratory work station (4) is moved into a X position in relation to the selected pipette tip carriers (2) for recording the digital images (12) with the digital camera (9).

16. The method according to claim 13, characterized in that the digital camera (9) has a field of view which in the Y direction of the Cartesian coordinate system deviates by at least a second angle, preferably by a third angle and in the X direction of the Cartesian coordinate system deviates by at least a fourth angle.

17. The method according to claim 16, characterized in that the digital camera (9) has the field of view in which the second angle is 14°, the third angle is 24°, and the angle is 18°.

18. The method according to claim 12, characterized in that the robot arm (7) with the digital camera (9) fastened thereon is positioned such that all of the selected pipette tip carriers (2) of a carrier (20) set up in the work area (3) of the laboratory work station (4) are in view of the digital camera (9) for three pipette tip carriers (2).

19. The laboratory work station (4) for carrying out the method according to claim 1, wherein the laboratory work station (4) comprises the work area (3) on which the selected pipette tip carriers (2) are disposed, wherein each of the selected pipette tip carriers (2) comprises the carrier plate (5) with an orthogonal arrangement of receiving holes (6) in which respectively one disposable pipette tip (1) can be inserted, wherein the laboratory work station (4) comprises the robot arm (7) with at least one pipette (8), which is configured for receiving and delivering liquid samples and for receiving and discarding disposable pipette tips (1), and wherein the laboratory work station (4) comprises the digital camera (9) which is disposed on the carrier device (10) and which is operatively connected to the evaluation unit (11) and with which the work area (3) of the laboratory work station (4) can be imaged completely at least in one direction, characterized in that the robot arm (7) of the laboratory work station (4) is simultaneously configured as the carrier device (10) for the digital camera (9), wherein the digital camera (9) has an optical axis (16) which passes through the carrier plate (5) of the selected pipette tip carriers (2) disposed on the work area (3) of the laboratory work station (4) at a first angle, wherein the first angle is 40° to 90°, and the digital camera (9) is attached to the robot arm (7) of the laboratory work station (4) such that all of the selected pipette tip carriers (2) of a carrier (20) set up in the work area (3) of the laboratory work station (4) can be recorded with only one image for three pipette tip carriers (2).

20. The laboratory work station (4) according to claim 19, characterized in that the first angle is 55° to 90°.

21. The laboratory work station (4) according to claim 19, characterized in that the first angle is 68°.

22. The laboratory work station (4) according to claim 19, characterized in that the work area (3) of the laboratory work station (4) forms a horizontal plane which is spanned between the X and Y axes of a Cartesian coordinate system.

23. The laboratory work station (4) according to claim 22, characterized in that the digital camera (9) has a field of view which deviates in the Y direction of the Cartesian coordinate system by at least a second angle, preferably by a third angle, and deviates in the X direction of the Cartesian coordinate system by at least a fourth angle.

24. The laboratory work station (4) according to claim 23, characterized in that the second angle is 14°, the third angle is 24° and the fourth angle is 18°.

25. The laboratory work station (4) according to claim 19, characterized in that the evaluation unit (11) is operatively connected to a controller (19) of the laboratory work station (4) or is integrated in the controller (19).

\* \* \* \* \*

UNITED STATES PATENT AND TRADEMARK OFFICE
CERTIFICATE OF CORRECTION

| | | |
|---|---|---|
| PATENT NO. | : 10,168,346 B2 | Page 1 of 1 |
| APPLICATION NO. | : 15/310269 | |
| DATED | : January 1, 2019 | |
| INVENTOR(S) | : Martin Schmidt and Rainer Kerkmann | |

It is certified that error appears in the above-identified patent and that said Letters Patent is hereby corrected as shown below:

On the Title Page

(71) Applicants Should read as: TECAN TRADING AG, Mannedorf (CH)

Signed and Sealed this
Fourth Day of February, 2020

Andrei Iancu
*Director of the United States Patent and Trademark Office*